(12) United States Patent
Thai et al.

(10) Patent No.: US 11,008,239 B2
(45) Date of Patent: May 18, 2021

(54) ALGAE SCRUBBER WITH DIRECTED WATER FLOW

(71) Applicant: SEA VOLUTE, LLC, Gainsville, VA (US)

(72) Inventors: Ari Thai, Fairfax, VA (US); Thuyet Huu Nguyen, Burke, VA (US)

(73) Assignee: SEA VOLUTE, LLC, Gainesville, VA (US)

( * ) Notice: Subject to any disclaimer, the term of this patent is extended or adjusted under 35 U.S.C. 154(b) by 282 days.

(21) Appl. No.: 15/546,176

(22) PCT Filed: Jan. 26, 2016

(86) PCT No.: PCT/US2016/014870
§ 371 (c)(1),
(2) Date: Jul. 25, 2017

(87) PCT Pub. No.: WO2016/123077
PCT Pub. Date: Aug. 4, 2016

(65) Prior Publication Data
US 2018/0029908 A1 Feb. 1, 2018

Related U.S. Application Data

(60) Provisional application No. 62/108,045, filed on Jan. 26, 2015.

(51) Int. Cl.
*A01G 33/00* (2006.01)
*C02F 3/32* (2006.01)
(Continued)

(52) U.S. Cl.
CPC .............. *C02F 3/322* (2013.01); *A01G 33/00* (2013.01); *C02F 3/32* (2013.01); *C12M 21/02* (2013.01);
(Continued)

(58) Field of Classification Search
CPC ............ C02F 3/32; C02F 3/322; A01G 33/00; C12M 21/02; Y02A 40/88; A01K 63/04; A01K 63/045; A01K 63/047
(Continued)

(56) References Cited

U.S. PATENT DOCUMENTS 3,462,360 A * 8/1969 McKinney ............ C02F 3/1257
210/602
4,690,128 A * 9/1987 Gibbons ................. F24S 60/00
126/705
(Continued)

FOREIGN PATENT DOCUMENTS

GB 2469198 10/2010
WO WO 2014/201298 12/2014

OTHER PUBLICATIONS

International Search Report for PCT/US2016/014870, dated May 2, 2016, 2 pages.
(Continued)

*Primary Examiner* — Christopher D Hutchens
*Assistant Examiner* — Brady W Frazier
(74) *Attorney, Agent, or Firm* — Nixon & Vanderhye, P.C.

(57) ABSTRACT

A water filtering system is provided for growing algae that filters the water. The system may include a container having a cylindrical inner surface and an opening at one end of the container. A clear central core including a cavity may be disposed inside the container and a light source may be disposed inside the cavity of the clear central core. A screen mesh may be disposed inside the container such that a surface of the screen mesh is parallel to the cylindrical inner surface of the container. The system may include an inlet configured to route water into the container and an outlet
(Continued)

configured to route water from the container. A lid may cover the opening of the container.

17 Claims, 12 Drawing Sheets

(51) Int. Cl.
*C12M 1/00* (2006.01)
*C02F 101/10* (2006.01)
*C02F 101/20* (2006.01)
*C02F 103/20* (2006.01)
*C02F 101/16* (2006.01)

(52) U.S. Cl.
CPC .... *C02F 2101/105* (2013.01); *C02F 2101/16* (2013.01); *C02F 2101/163* (2013.01); *C02F 2101/166* (2013.01); *C02F 2101/20* (2013.01); *C02F 2103/20* (2013.01); *C02F 2301/026* (2013.01); *Y02A 40/80* (2018.01)

(58) Field of Classification Search
USPC .............. 47/1.4; 210/167.21, 167.22
See application file for complete search history.

(56) References Cited

U.S. PATENT DOCUMENTS

| | | | | |
|---|---|---|---|---|
| 5,098,585 | A * | 3/1992 | Woltman | A01K 63/045 119/259 |
| 5,636,472 | A * | 6/1997 | Spira | A01G 31/02 210/150 |
| 5,728,293 | A | 3/1998 | Guoli et al. | |
| 5,935,516 | A * | 8/1999 | Baugh | A01G 9/00 128/205.26 |
| 6,837,991 | B1 | 1/2005 | Norris | |
| 7,578,933 | B1 * | 8/2009 | Selman | A01K 63/04 119/260 |
| 8,017,366 | B1 | 9/2011 | Schuh et al. | |
| 8,262,776 | B2 | 9/2012 | Hazlebeck et al. | |
| 8,940,531 | B2 | 1/2015 | Seong | |
| 9,003,695 | B2 | 4/2015 | Oyler | |
| 9,005,918 | B2 | 4/2015 | Dvorak et al. | |
| 9,040,283 | B2 | 5/2015 | Muller-Feuga | |
| 9,045,724 | B2 | 6/2015 | Roux Dit Buisson | |
| 9,051,539 | B2 | 6/2015 | Snyder et al. | |
| 9,057,043 | B2 | 6/2015 | Flynn et al. | |
| 9,102,923 | B2 | 8/2015 | Meiser et al. | |
| 9,145,539 | B2 | 9/2015 | Turner et al. | |
| 2005/0109695 | A1 * | 5/2005 | Olivier | A01K 63/04 210/605 |
| 2010/0276361 | A1 * | 11/2010 | Limcaco | C02F 3/32 210/602 |
| 2012/0252103 | A1 * | 10/2012 | Deane | A01G 33/00 435/257.1 |
| 2013/0133250 | A1 * | 5/2013 | Chan | B01D 21/262 47/1.4 |
| 2013/0233779 | A1 | 9/2013 | Farrish | |
| 2013/0280757 | A1 * | 10/2013 | Dvorak | C12M 21/02 435/41 |
| 2016/0281041 | A1 * | 9/2016 | Wilson | A01K 63/06 |

OTHER PUBLICATIONS

Written Opinion of the ISA for PCT/US2016/014870, dated May 2, 2016, 7 pages.
"Inflow Algae Scrubber", *CDMills Designs*, http://cdmillsdesigns.blogspot.com/2013/01/latest-update-on-my-ias-11-design.html, 4 pages.
"The Turbo L4 Algae Scrubber (obsolete)", *Algae Scrubbing*, https://www.algaescrubbing.com/threads/the-turbo-14-algae-scrubber-obsolete.41/, Nov. 2012, 14 pages.
"HOG.5 Hang-On-Glass UAS Upflow Algae Scrubber—1/2 Cube feeding per day", *Santa Monica Filtration*, http://www.santa-monica.cc/HOG5-Hang-On-Glass-UAS-Upflow-Algae-Scrubber-12-Cube-feeding-per-day_p_21.html, 6 pages.

* cited by examiner

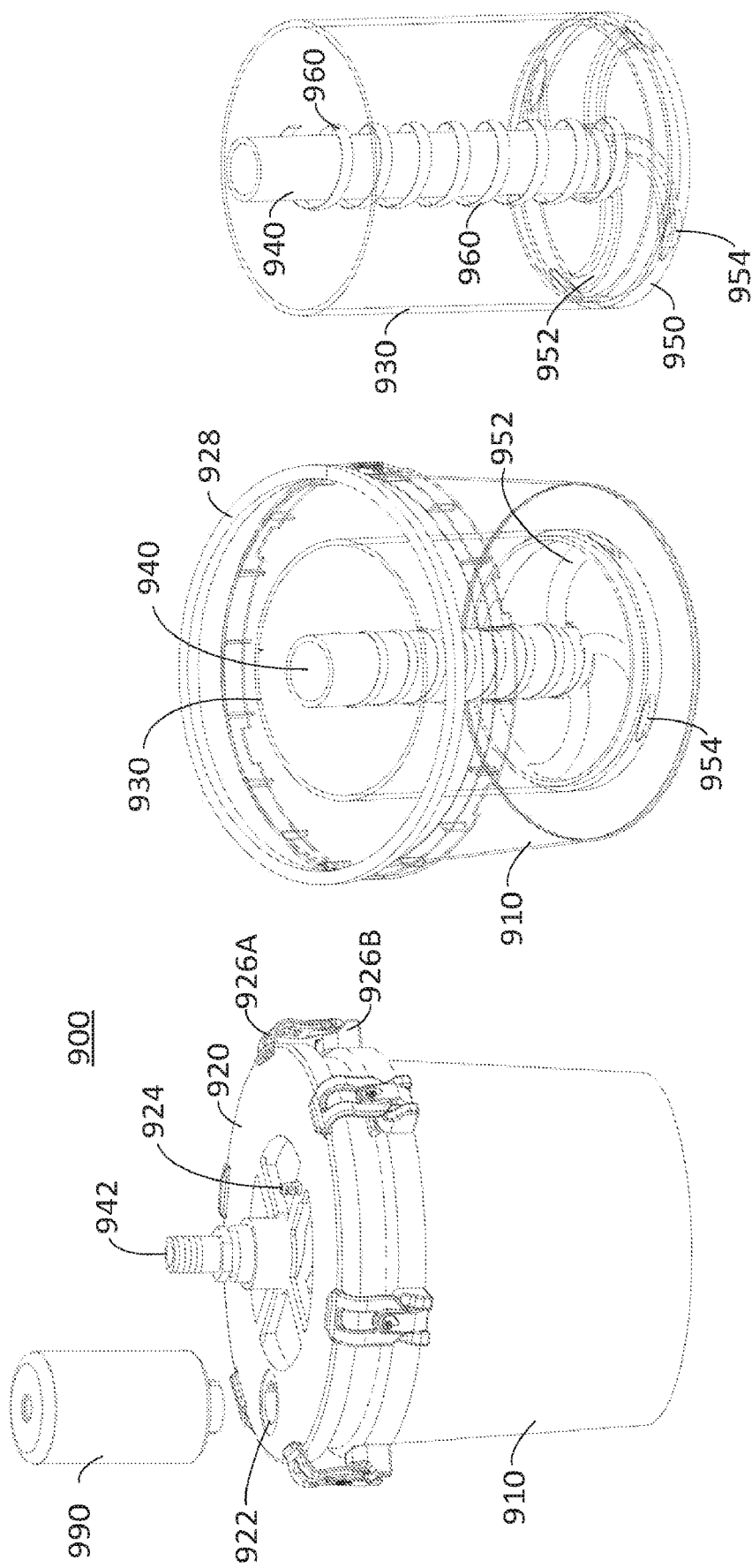

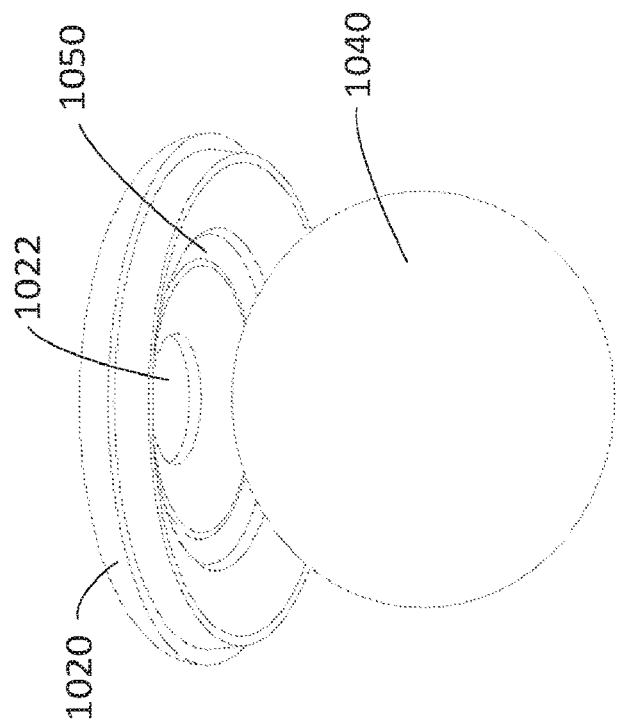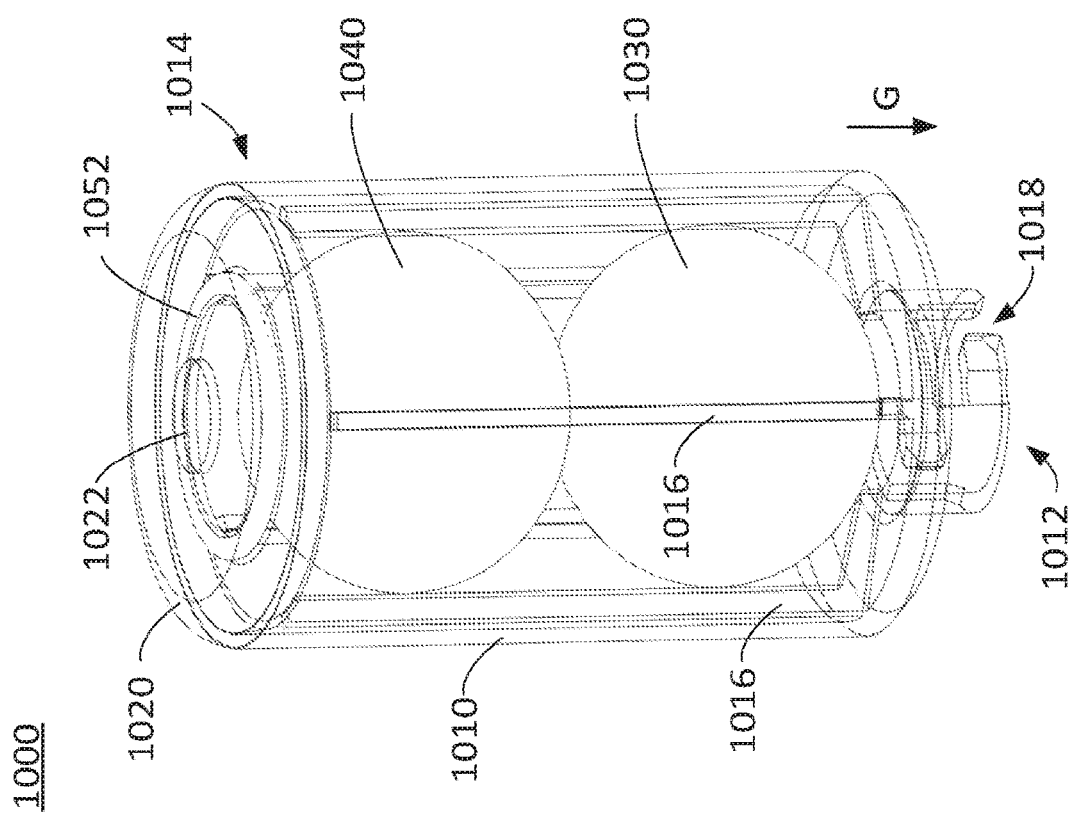

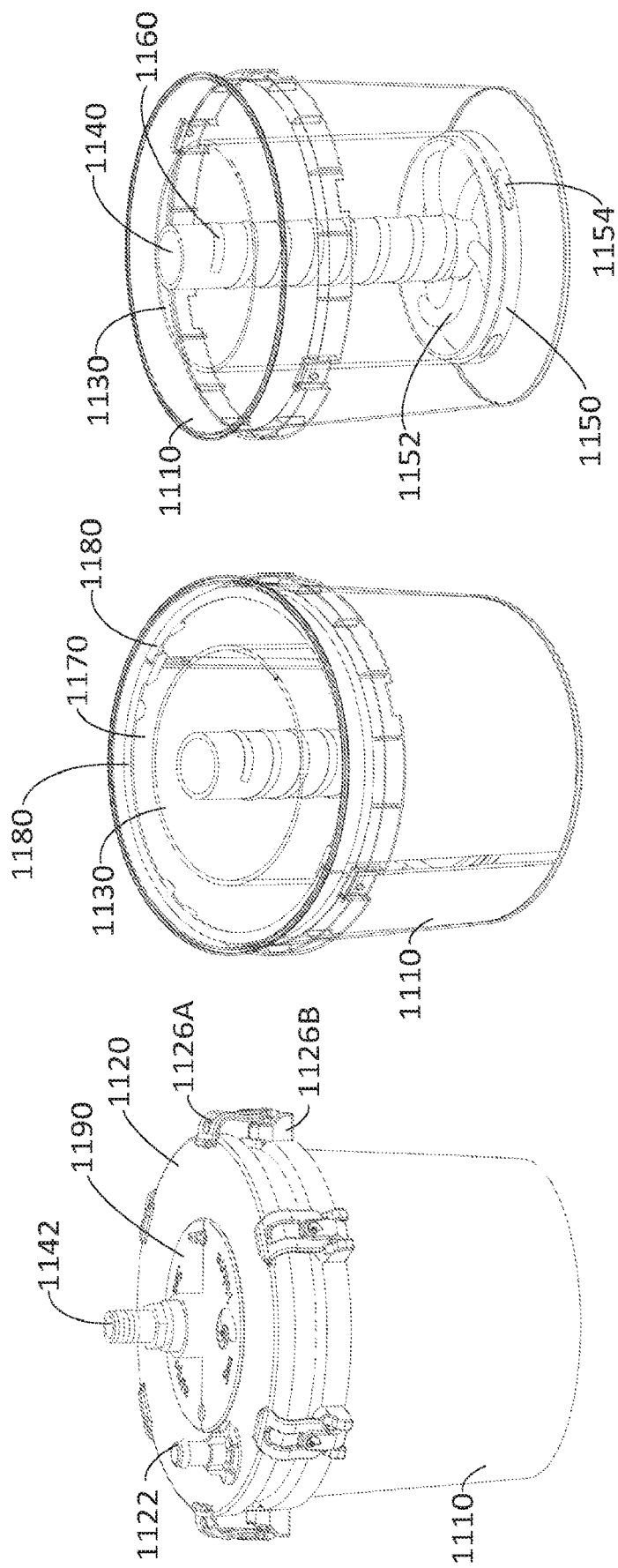

ALGAE SCRUBBER WITH DIRECTED WATER FLOW

CROSS-REFERENCES TO RELATED APPLICATIONS

The present application is the U.S. national phase of International Application No. PCT/US2016/014870 filed Jan. 26, 2016, which designated the U.S. and claims priority to U.S. Provisional Application No. 62/108,045, filed on Jan. 26, 2015, the entirety of which are incorporated by reference herein.

BACKGROUND

The subject matter of this application is directed to filtration systems and more particularly to filtration systems that employ biological organisms, such as algae, to process water contaminants.

Algae in ponds, rivers, lakes, and oceans, processes and removes nutrients and chemicals from the water. More recently hobbyists have introduced algae based filtration systems to filter saltwater aquariums, freshwater aquariums, and ponds. These algae based filtration systems, sometimes referred to as algae scrubbers, provide a controlled environment for algae to grow and for the algae to filter the water.

A typical algae scrubber includes a surface to which water and light are provided. The water brings nutrients to the algae growing on the surface and the light promotes photosynthesis by the algae which causes the algae to grow and consume the nutrients in the water. The flow speed of the water on the surface is an important factor for efficient growth of the algae because the flow of the water needs to be strong enough to push away the static layer of water that is close to the surface of the algae (called a boundary layer). Faster flow speed of the water maintains a thinner boundary layer, which causes nutrients in the water to be transferred quicker to the algae via diffusion through the boundary layer.

In one design of an algae scrubber (see U.S. Pat. No. 6,837,991), a partially submerged rotatable drum wrapped in plastic mesh or algae screen is rotated while water is forced to pass directly through the algae screen. One disadvantage of this design is that, as algae grows thicker on the mesh of the drum, the drum will become heavier and cause the rotation of the drum to slow down. Slowing the rotation of the drum will reduce the efficiency of the algae growth due to the changes in the water flow. In addition, with enough algae growth the drum may get stuck. Furthermore, the rotation of the drum may cause undesirable noise and movement of water.

In another design of an algae scrubber, a "waterfall" model is used to cause water driven by gravity to flow over a mesh. The water is provided via a slot cut along the length of a pipe, which is suspended horizontally above the mesh. A major disadvantage of the "waterfall" model is that a large amount of space is required for the algae scrubber. Specifically, the algae scrubber with the waterfall model needs to be placed above a sump for the sump to collect the water exiting at the bottom of the algae scrubber via gravity.

Other designs of an algae scrubber utilize bubbles to bring nutrients and water turbulence to an algae screen. However, such designs are noisy due to the operation of the air pumps. In addition, the algae screen in this design is constrained to a small area where the bubbles are generated by an air pump.

BRIEF DESCRIPTION OF THE DRAWINGS

So that features of the present invention can be understood, a number of drawings are described below. It is to be noted, however, that the appended drawings illustrate only particular embodiments of the invention and are therefore not to be considered limiting of its scope, for the invention may encompass other equally effective embodiments.

FIGS. 9A-9C illustrate a filter system for growing algae according to another embodiment of this disclosure.

FIGS. 10A and 10B illustrate a ball valve assembly according to one embodiment of this disclosure.

FIGS. 11A-11C illustrate a filter system for growing algae according to another embodiment of this disclosure.

DETAILED DESCRIPTION

Figure 1:
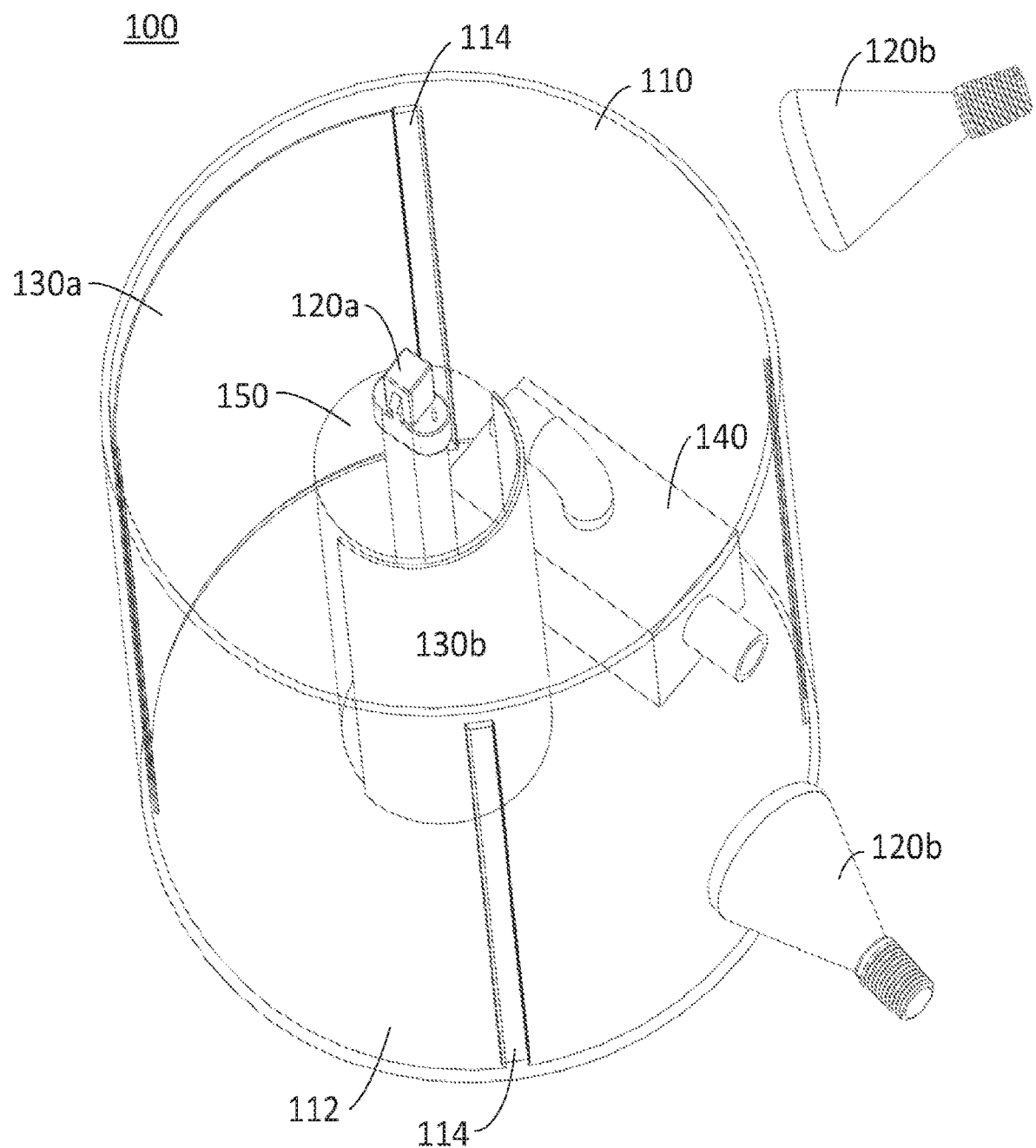
FIG. 1 illustrates a filter system for growing algae according to one embodiment of this disclosure.

The present disclosure provides systems and methods to employ biological organisms such as algae to filter water. Such systems and method may be used to filter, for example, freshwater and saltwater aquariums, ponds, and effluent from agricultural, human, animal and industrial sources. Filtering refers to the algae's ability to adhere to and/or filter water by physical methods and also refer to the algae's ability to consume undesirable chemicals in the water such as nitrate, phosphate, nitrite, ammonia, ammonium and even metals such as copper.

Certain example embodiments relate to a system for growing algae. The system may include a container, a light source directing light at a surface inside the container, and a pressurized mechanism to push a portion of the water inside the container to create an entrainment effect to create a generally circular or spiral flow of water inside the container and over the surface. The surface may be meant for algae to grow on. For example, the surface may be further coated, embedded, textured or perforated for algae growth.

Certain example embodiments relate to a water filtering system for growing algae that filters the water. The system may include a container having a cylindrical inner surface and an opening at one end of the container. A clear central core including a cavity may be disposed inside the container and a light source may be disposed inside the cavity of the clear central core. A screen mesh may be disposed inside the container such that a surface of the screen mesh is parallel to the cylindrical inner surface of the container. The system may include an inlet configured to route water into the container and an outlet configured to route water from the container. A lid may cover the opening of the container.

Certain example embodiments relate to a bioremediation water filtering apparatus. The apparatus may include a cylindrical container, an inlet assembly for providing water into the cylindrical container, and a lid covering the cylindrical container and including an outlet for removing the water from the cylindrical container. A light source may be disposed inside the cylindrical container and a screen mesh may be disposed inside the cylindrical container and parallel to an inner side surface of the cylindrical container for growing algae for bioremediation of the water.

The systems and methods of this disclosure provide for a filtration system that efficiently removes undesired nutrients and/or chemicals from water without requiring additional chemicals to perform the filtration. Additional chemicals are often used to convert undesired nutrients and/or chemicals to a less undesirable form or to precipitate undesirable chemicals from solution (i.e., water). The embodiments of this application provide for systems that are quiet and reduce, and in some cases eliminate, moving parts. Embodiments of this application also provide for a compact filtration system that is not restricted to the locations where it can be placed.

The systems and methods of this disclosure is designed both to eliminate or supplement the use of additional physical and/or chemical methods for filtration and removal of undesirable nutrients and/or chemicals. When the systems and methods of this disclosure is working in conjunction with other filtration methods, it can work in parallel or in series, or both. Working in series refers to using the systems and methods of this disclosure as a pretreatment process, or a posttreatment process for conventional physical/chemical/biological filtration processes.

Other objectives and advantages of the present invention will become apparent to the reader and it is intended that these objectives and advantages are within the scope of the present disclosure.

FIG. 1 illustrates a filter system 100 for growing algae according to one embodiment of this disclosure. The filter system 100 may include a container 110, a surface 130a and/or 130b, a light source 120a and/or 120b, and a pressurized mechanism 140.

The surface 130a may be disposed inside the container 110 and against a side wall of the container 110. The surface 130a may be provided parallel to an inside surface of the container 110. The surface 130b may be disposed inside the container 110 and a certain distance away from the side wall of the container 110. The surface 130b may be provided parallel to the inside surface of the container 110. As shown in FIG. 1, the light source may be provided inside the container 110 (e.g., see light source 120a) and/or outside of the container 110 (e.g., see light source 120b). The light source 120b outside of the container 110 may be provided such that the light from the light source 120b enters the container 110 through the side surface of the container 110, the bottom surface of the container 110, and/or the top surface of the container 110 (e.g., a lid), one or more of which may partially or completely transparent. The light from the light source 120b may enter through the top of the container 110 that is not covered by a lid. The light source 120a and/or 120b may be positioned such that the light from the light sources 120a and/or 120b is provided to the surface 130a and/or 130b. The pressurized mechanism 140 may be disposed inside or outside of the container 110 to create a flow of water inside the container 100 and over the surface 130a and/or 130b.

The filter system 100 allows for a fast water flow to be created over the surface 130a and/or 130b. The filter system 100 may filter the water that is stored in the container 110 or the water may be provided inside the container via one or more inlets and/or one or more outlets discussed with reference to other embodiments of this disclosure. The pressurized mechanism 140 may push a portion of the water inside the container to create an entrainment effect providing a generally circular or spiral flow of water inside the container 110 and over the surface 130a and/or 130b. The entrainment effect provides for fast water flow to be generated over the all portions of the surface 130a and/or 130b without needing a specific path being defined for the water flow.

The filter system 100 may filter water by moving water rapidly over the surface 130a and/or 130b, which is illuminated by the light source 120a and/or 120b. The combination of the water flow and light provide for algae to grow on the surface 130a and/or 130b. The algae on the surface 130a and/or 130b consumes nutrients in the water (e.g., nitrate, phosphate, nitrite, ammonia, ammonium, $CO_2$) and may consumer metals such as copper in the water. The filter system 100 allows for the algae to be grown in a controlled environment, allowing for algae grown in other parts of the system (e.g., aquarium or pond) to be discouraged. In addition, the filtration of the water performed by the algae also reduces nutrients in the water that may cause sickness in fish, invertebrates, and corals. The growth of algae on the surface 130a and/or 130b may also allow for the algae to maintain desired oxygen levels and help to buffer pH by preventing high levels or carbon dioxide from building up in the system.

Algae grown on the surface 130a and/or 130b may be periodically removed to allow for new algae growth. The algae may be removed when the algae fills the surface 130a and/or 130b, when the algae starts to turn dark, or when undesired nutrients start to rise in the water. It may be desirable to remove the algae before the algae on the surface 130a and/or 130b becomes too thick so that light and water may penetrate the majority of the algae on the surface 130a and/or 130b. The algae may be scraped from the surface 130a and/or 130b. The surface 130a and/or 130b may be removed from the filter system 100 to scrape the algae from the surface 130a and/or 130b.

The container 110 may be a generally cylindrical container including a bottom surface 112 and/or a top surface (not shown in FIG. 1). The bottom surface 112 and/or the top surface may be permanently attached to respective ends of the side wall of the cylindrical container or may be removably coupled to the container 110 to enclose the container 110. The container 110 may be a transparent cylindrical container. The bottom surface 112 and/or the top surface may be made of a transparent material. The container 110 may be made of plastic (e.g., acrylic) or glass such that light may pass through the side wall of the container 110 and reach the surfaces 130a and/or 130b inside the container 110. In one embodiment, the side wall of the container 110 may be transparent while the bottom surface 112 and/or the top surface may be non-transparent. In one embodiment, the container 110 may be coated or made of a material that does not allow for light to enter from outside of the container 110.

The container 110 may further include an inner core 150 disposed inside the container 110. The inner core 150 may reduce the amount of water to be circulated inside the container and thereby help to speed up the flow of the water inside the container 110. The speed of the water flow due to the presence of the inner core 150 may be needed to push away the static layer of water that is close to the surface of the algae, allowing nutrients in the water to be effectively transferred to the algae.

The inner core 150 may have a cylindrical shape and be disposed approximately in the middle of the container 110. The inner core 150 may be disposed such that the side surface of the inner core 150 is provided approximately parallel to the side surface of the container 110. In one embodiment, the inner core 150 may be a solid volume. The inner core 150 and the container 110 may be positioned such that they share the same vertical axis.

The inner core 150 may include a cavity for the light source 120*a* to be disposed inside the cavity. The inner core 150 may be made of a transparent material (e.g., glass or plastic) to allow the light from the light source 120*a* to be provided to the surface 130*a* and/or 130*b* inside the container 110. In one embodiment the inner core 150 may be a transparent plastic tube. The inner core 150 may be part of the container 110 or may be removably coupled to the bottom surface 112 of the container 110. The inner core 150 may have a solid surface and the cavity of the inner core 150 may be sealed from inside of the container 110 such that water provided inside the container does not enter the cavity. In one embodiment, the inner core 150 may have a permeable surface and the light source 120*a* disposed inside the cavity of the inner core 150 may be submersible in water.

As shown in FIG. 1, the inside surface of the container 110 may include one or more protrusions 114 that provide grooves to secure the surface 130*a* against or next to the inside surface of the container 110. A plurality of different sections of the surface 130 (e.g., four different section in the embodiment shown in FIG. 1) may be provided adjacent to the inside surface of the container 110. In one embodiment, the surface 130*a* may be a single section that wraps around the inside surface of the container 110.

The surface 130*b* may be disposed against or next to the outside surface of the inner core 150. The surface 130*b* may be a single section having a shape that is similar to the outside surface of the inner core 150. In one embodiment, the surface 130*b* may include a plurality of sections that are secured to the surface of the inner core 150 (e.g., via one or more protrusions providing groves to secure the surface 130*b*). As shown in FIG. 1, the surface 130*b* may be provided such that it is parallel to the inner surface of the container 110.

The surface 130*a* and/or 130*b* may be made of a material (e.g., plastic) that facilitates growth of algae. The surface 130*a* and/or 130*b* may be permeable for nitrifying and photosynthesizing algae. In one embodiment, the surface 130*a* and/or 130*b* may be a flexible mesh and/or resilient mesh to allow the surface 130*a* and/or 130*b* to conform to the surface of the container 110 and/or inner core 150. The surface 130*a* and/or 130*b* may be provided with a specific texture that is designed to promote algae growth. In one embodiment, the surface 130*a* and/or 130*b* may be provided with application of live algae to expedite growth of the algae during initial installation of the system 100.

The light source 120*a* and/or 120*b* may be one or more of LEDs, florescent bulbs, and/or halogen bulbs, but are not so limited. The light source 120*a* and/or 120*b* may be configured to provide light with a specific spectrum that promotes algae growth. In one embodiment, the spectrum of the light source can be adjustable to allow the user to select the desired type of light to be provided to the surface 130*a* and/or 130*b*. The light source 120*a* may include one or more different light sources that provide light in all directions to the inside surface of the container 110. The light source 120*b* may be one or more light sources that provide lights in all directions of the outside surface of the container 110 (on the sides and/or top and bottom of the container 110). In one embodiment, the light source 120*a* and/or 120*b* may be LED strip lighting. The LED strip lighting may be flexible and/or submersible in water. The LED strip lighting may be wound around the outside or inside surface of the container 110 and/or the inside or outside surface of the inner core 150.

The pressurized mechanism 140 may be a pump that provides and/or circulates the water inside the container 110. The pressurized mechanism 140 may provide a high-pressured input flow that directly generates a circular or spiral flow in the container 110. The pressurized mechanism 140 may have an inlet configured to receive water from inside of the container 110 and/or from an outside source (e.g., an overflow tank or fish tank) and an outlet configured to move water into the container 110. As will be discussed in more detail below, the outlet may have a shape that moves the water in a circular direction inside the container 110. In one embodiment, the water may be provided inside the container 110 via the pressurized mechanism 140 coupled to an inlet in the container (e.g., inlet 250 shown in FIG. 2) and removed as the water overflows over the rim of the container 110 or via an outlet (not shown in FIG. 1) in the container 110 or a lid of the container (not show in FIG. 1). While the pressurized mechanism 140 is shown inside the container and at a bottom surface of the container 110, the location of the pressurized mechanism 140 is not so limited. The pressurized mechanism 140 may be provided outside of the container 110, inside the cavity of the inner core 150, or adjacent to an outside surface of the container 110.

In some embodiments, an inlet to provide water inside the container 110 may be provided as part of the container 110 and the pressurized mechanism 140 may be removably coupled to the inlet. An outlet (not shown in FIG. 1) may be provided in the container 110 to remove water from inside the container. In some embodiments, the pressurized mechanism 140 may include an air pump that introduces air bubbles into the water provided inside the container 110.

Figure 2:
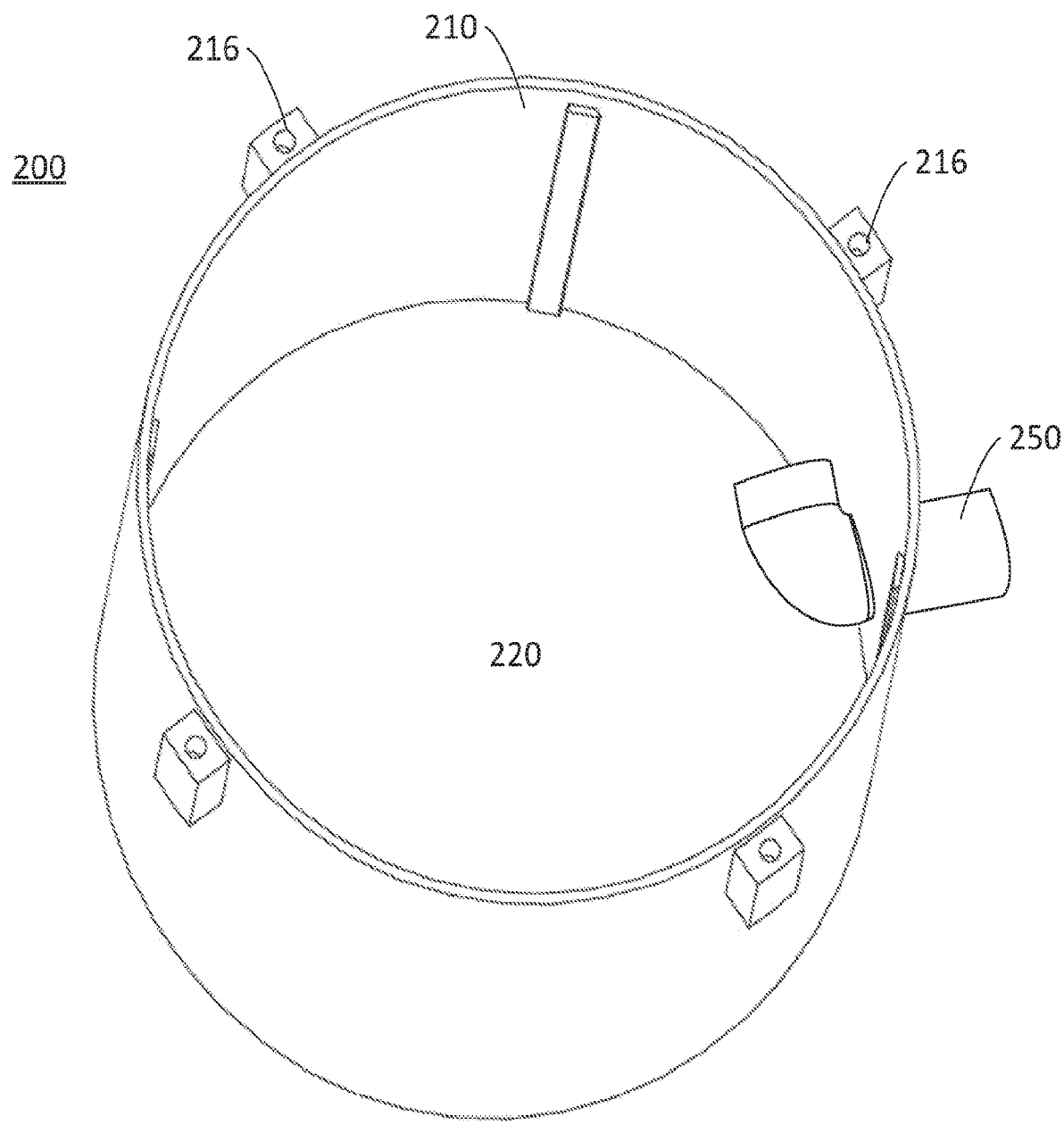
FIG. 2 illustrates a filter system for growing algae according to another embodiment of this disclosure.

FIG. 2 illustrates a filter system 200 for growing algae according to another embodiment of this disclosure. The filter system 200 includes a cylindrical container 210 with a bottom surface 220 and an inlet 250 provided on the side surface of the cylindrical container 210. The end of the inlet 250 outside of the container 210 may be coupled to a pump providing high pressured flow of water or coupled to a pressurized water flow due to gravity. The inlet 250 may allow for water flow inside the container 210 and generate a circular flow of water. The circular flow of water inside the container 210 may generate a vortex inside the container 210. As shown in FIG. 2, the inlet 250 may have an elbow inside the container 210 to provide the circular flow of water along the inside surface of the container 210. The elbow may have a 90 degree angle. In another embodiment, the elbow may have a 135 degree angle. In another embodiment, the inlet 250 may be provided in a bottom surface 220 or a lid (not shown in FIG. 2) covering the top of the container 210. The inlet 250 may be provided near the side surface of the container to more effectively generate the circular flow of water inside the container.

The container 210 may be covered with a lid (not shown in FIG. 2) which is secured to the container 210 via fastening portions 216 provided at one end of the container 210. The lid may include an outlet to remove water from the container 210. In other embodiments, the water may overflow over the rim of the container. The lid may provide for an air and water tight seal in the container 210. The lid with the air and water tight seal may help maintain pressure of the influent flow inside the container such that effluent flow can rise above the top of the container. As will be discussed in more detail below, the air and water tight seal of the lid may allow for the filter system 200 to be positioned at any location, even at locations that are higher than the water tank from which water is supplied.

Figure 3:
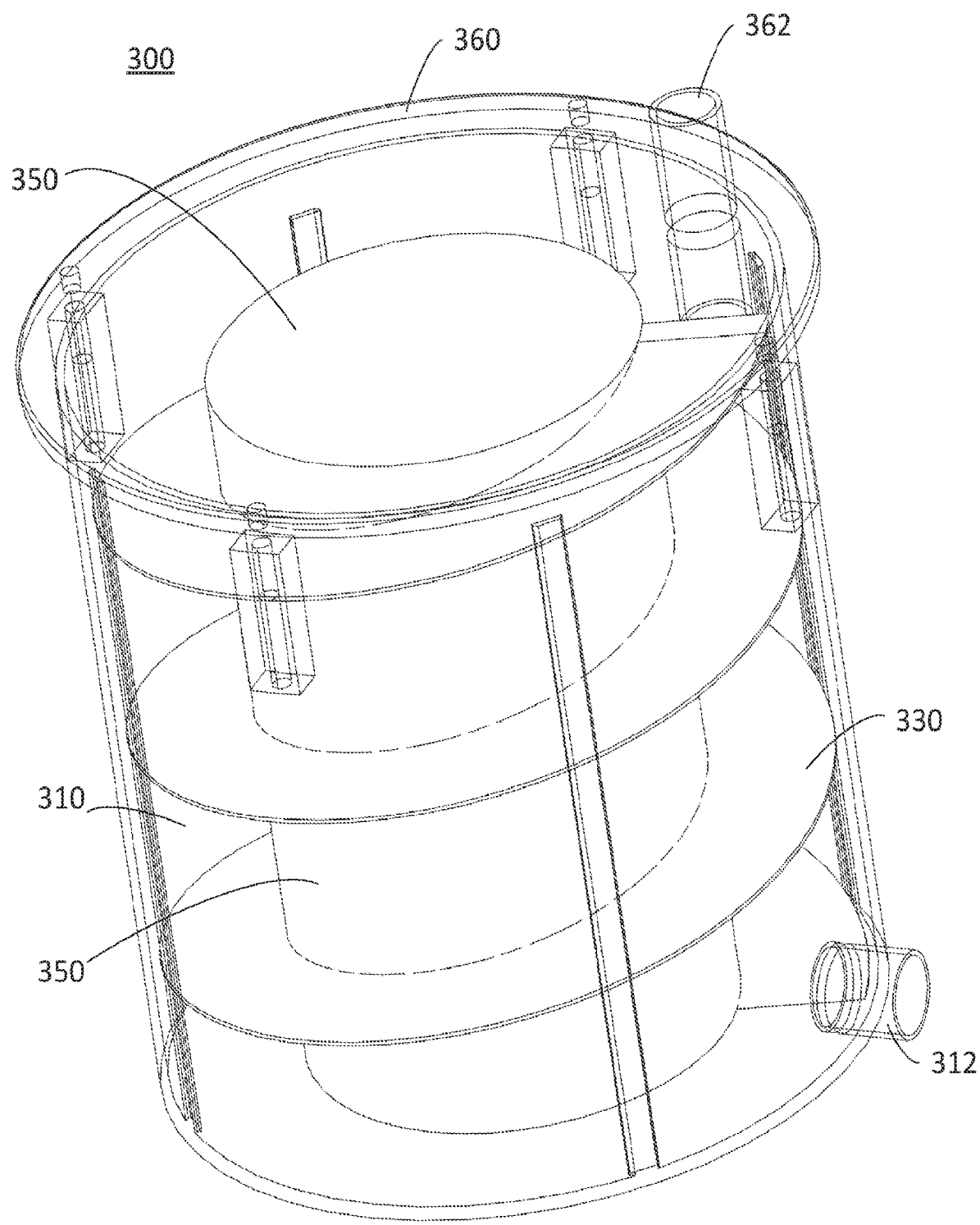
FIG. 3 illustrates a filter system for growing algae according to another embodiment of this disclosure.

FIG. 3 illustrates a filter system 300 for growing algae according to another embodiment of this disclosure. The filter system 300 may include a container 310, a surface 330, an inner core 350, a lid 360, an inlet 312, and an outlet 362. The container 310 may be a cylindrical container having an opening on one end. The lid 360 may be removably coupled (e.g., via a thread or clamps) to the open end of the container 310. The inlet 312 may allow for water to enter the container 310 and the outlet 362 may allow for water to be removed from the container 310. As shown in FIG. 3, the inlet 312 may be provided on a side surface of the container 310 and the outlet 362 may be provided in the lid 360. However, the location of the inlet 312 and/or the outlet 362 are not so limited.

The inner core 350 may be disposed inside of the container 310 and approximately in the middle of the container 310 with the side surface of the inner core 350 being parallel to the inner surface of the container 310. The inner core 350 may include a cavity for a light source to be disposed inside the cavity. A light source may be provided outside of the container 310. In one embodiment, inner core 350 may serve as a light conductor to transport light from a light source provided outside of the container 310 to the inside of the container 310. The light conductor may be an optical waveguide providing for internal reflection of the light until the light reaches the inside of the container 310, where the light is reflected onto the screen positioned inside of the container 310. A portion of the light conductor may be provided outside of the container to guide the light from the location of the light source (e.g., via an optical fiber). The inner core 350 may be solid and may include materials, such as acrylic resin, polycarbonate, epoxies, and/or glass. In one embodiment, the inner core 350 may be a light pipe transporting light from the light source positioned outside of the container 310 and inside of the container 310 where the light is distributed to the surface of screen.

As shown in FIG. 3, the surface 330 may be a spiral ramp surface disposed between the inside surface of the container 310 and the inner core 350. The spiral ramp surface may begin at the bottom of the container 310 and near the inlet 312, and extend upwardly and toward the rim of the container 310. The spiral ramp surface may create for a path for the water the flow inside the container and for algae to grow.

Figure 4:
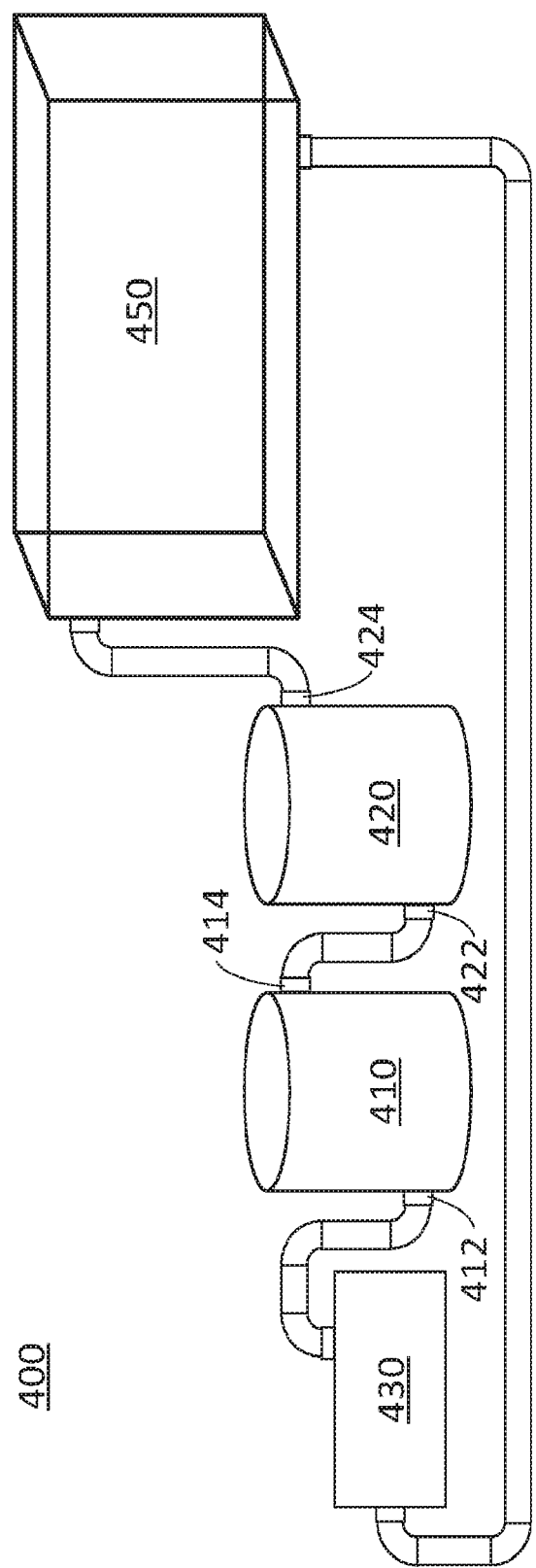
FIG. 4 illustrates a filter system including a plurality of filters according to an embodiment of this disclosure.

FIG. 4 illustrates a filter system 400 including a plurality of filters according to an embodiment of this disclosure. The filter system 400 may include a first algae filter 410 that is connected in series to a second algae filter 420.

A pressurized mechanism 430 may pump water from a water tank (e.g., an aquarium or a pond) 450 and supply the water to an inlet 412 in the first algae filter 410. The pressure created by the pressurized mechanism 430 may move the water inside of the first algae filter 410 and outside of the first algae filter 410 via the outlet 414. The outlet 414 of the first algae filter 410 may be coupled to an inlet 422 of the second algae filter 420 to provide the water from the first algae filter 410 to the second algae filter 420. The pressure created by the pressurized mechanism 430 may move the water inside of the second algae filter 420 and outside of the second algae filter 420 via the outlet 424. The outlet 424 of the second algae filter 420 may be coupled to the water tank 450 to supply water filtered by the first and second algae filters 410 and 420 to the water tank 450.

The air and water tight lids provided in the first and second algae filters 410 and 420 may allow for pressure generated by a single pressurized mechanism 430 to move water in both of the filters 410 and 420. In addition, the air and water tight lids may allow for the filters 410 and 420 to be positioned at any location, even at locations that are higher than the water tank 450.

The filter system 400 is not limited to the first and second algae filters 410 and 420 shown in FIG. 4, but may include a plurality of algae filters connected in daisy-chain and/or in parallel. In one embodiment, a separate pressurized mechanism 430 may be provided for each algae filter.

Figure 5:
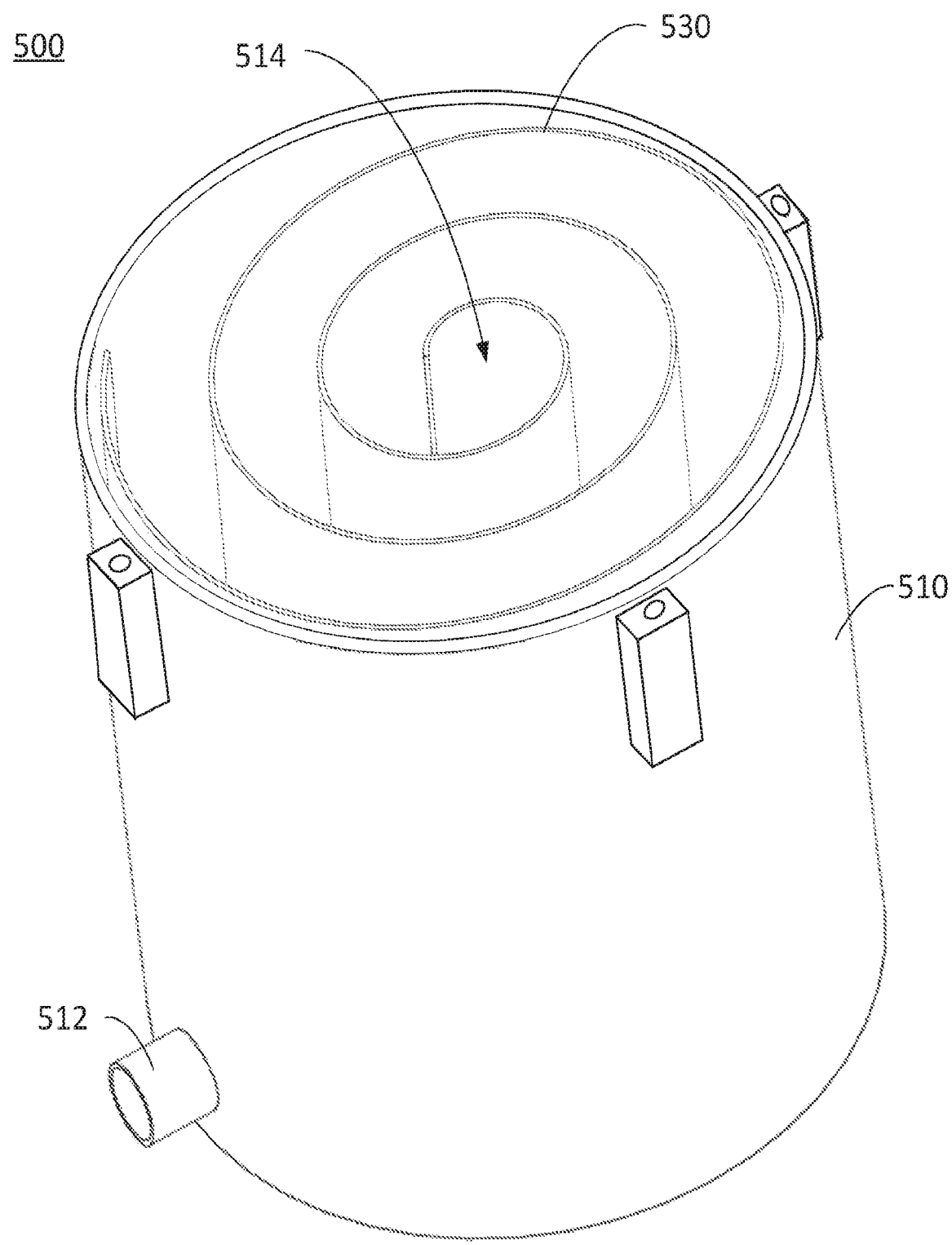
FIG. 5 illustrates a filter system for growing algae according to another embodiment of this disclosure.

FIG. 5 illustrates a filter system 500 for growing algae according to another embodiment of this disclosure. The filter system 500 may include a container 510, a spiral surface 530, and an inlet 512. The container 510 may be a cylindrical container having an opening on one end. A lid (now shown in FIG. 5) may be removably coupled (e.g., via a thread or clamps) to the open end of the container 510. The inlet 512 may allow for water to enter the container 510 and an outlet (not shown in FIG. 5) may allow for water to be removed from the container 510. As shown in FIG. 5, the inlet 512 may be provided on a side surface of the container 510 and at the bottom of the container 510. The outlet may be provided in the lid. However, the location of the inlet 512 and/or the outlet are not so limited.

As shown in FIG. 5, the spiral surface 530 may extend from the bottom of the container 510 to the rim of the container 510 and be provided such that the surface is parallel to the side surface of the container 510. The spiral surface 530 may start an inner surface of the container 510 and wind around a central axis of container 510 creating a path for the water to flow. The path may start at the edge of the container 510 (e.g., near the inlet 512) and finishes at the center 514 of the container 510 (e.g., near the outlet 514) where an outlet would allow for the water to exit the container 510. The created path may circle a plurality number of times around the axis of the cylindrical container 510. At the inner surface of the container 510, the spiral surface 530 may be positioned against the inner surface of the container 510 (e.g., via a grove provided by the container). The spiral surface 530 may be positioned against the bottom surface of the container 510 at one end and against the lid 560 at the other end to ensure that water provided inside of the container via the inlet 512 moves through the path created by the spiral surface 530.

Light may be provided to the spiral surface 530 via the lid 560 and/or the bottom of the container 510, which may be transparent to allow light to pass from outside of the container 510. The combination of the light and the flow of water via the path created by the spiral surface 530 will promote growth of algae on the spiral surface 530. The spiral surface 530 may be removable from inside of the container 510 for removal of the algae.

Figure 6:
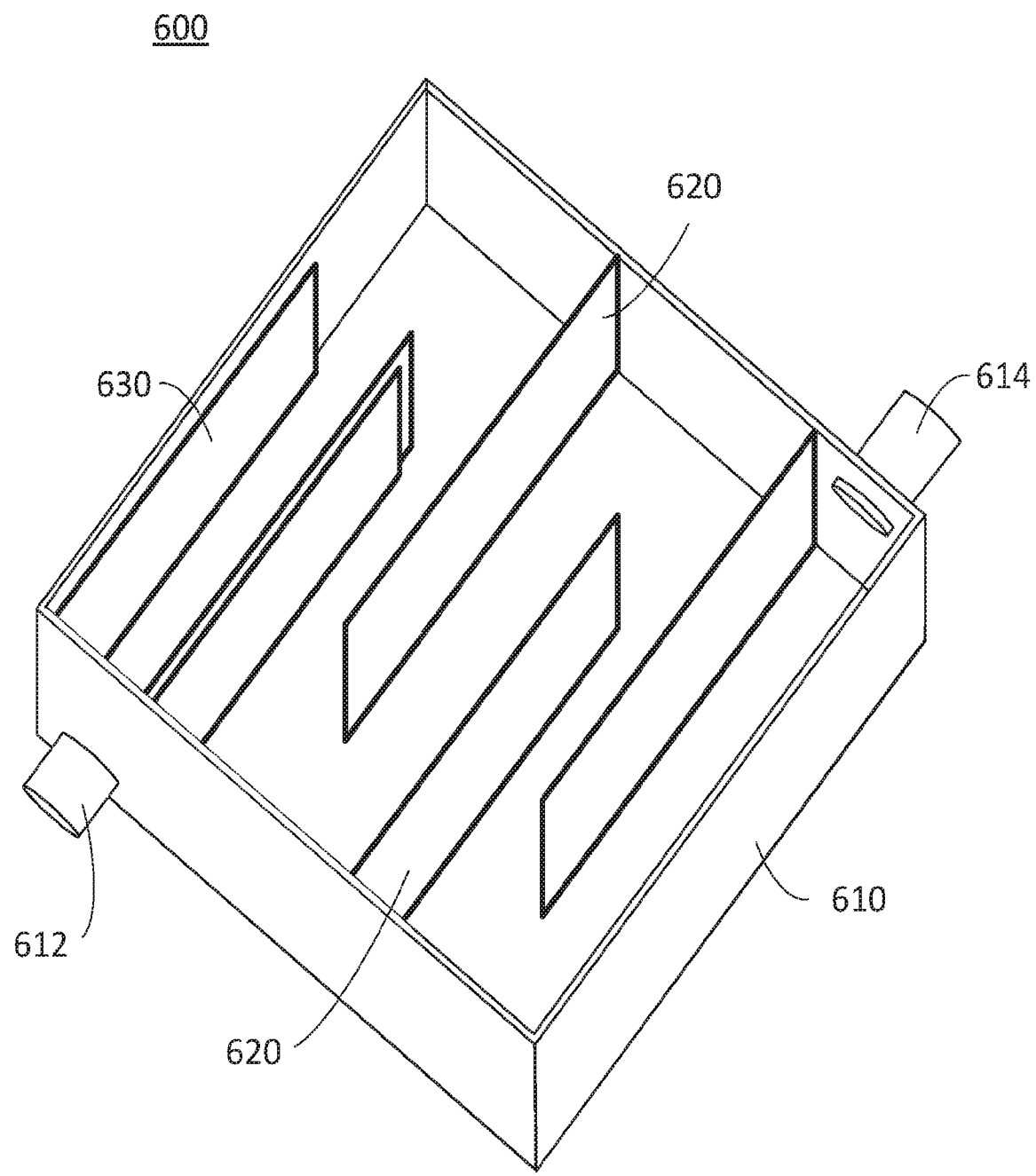
FIG. 6 illustrates a filter system for growing algae according to another embodiment of this disclosure.

FIG. 6 illustrates a filter system 600 for growing algae according to another embodiment of this disclosure. The filter system 600 may include a container 610, a plurality of flow guides 620, a plurality of algae screens 630, an inlet 612 and an outlet 614. The container 610 may have a square or rectangular shape with the inlet 612 provided at one corner of the container 610 and the outlet 614 provided at an opposite corner of the container 610. The plurality of flow guides 620 may be disposed inside of the container 610 to provide a flow path of the water inside of the container 610. The flow guides 620 may have a rectangular shape and be disposed parallel to each other and at least one surface of the container 610. The algae screens 630 may be positioned inside of the container 610 and against the surface of the container 610 and/or the flow guides 620. A lid (not shown in FIG. 6) may cover the container 610 to provide an air and water tight seal.

Light may be provided to the algae screens from outside of the container 610 via a transparent lid and/or transparent bottom surface of the container 610. In one embodiment, a light source may be provided inside of the container 610. The combination of the light and the flow of water via the path created by the flow guides 620 will promote growth of algae on the algae screens 630. The algae screens 630 may be removable from inside of the container 610 for removal of the algae.

Figure 7:
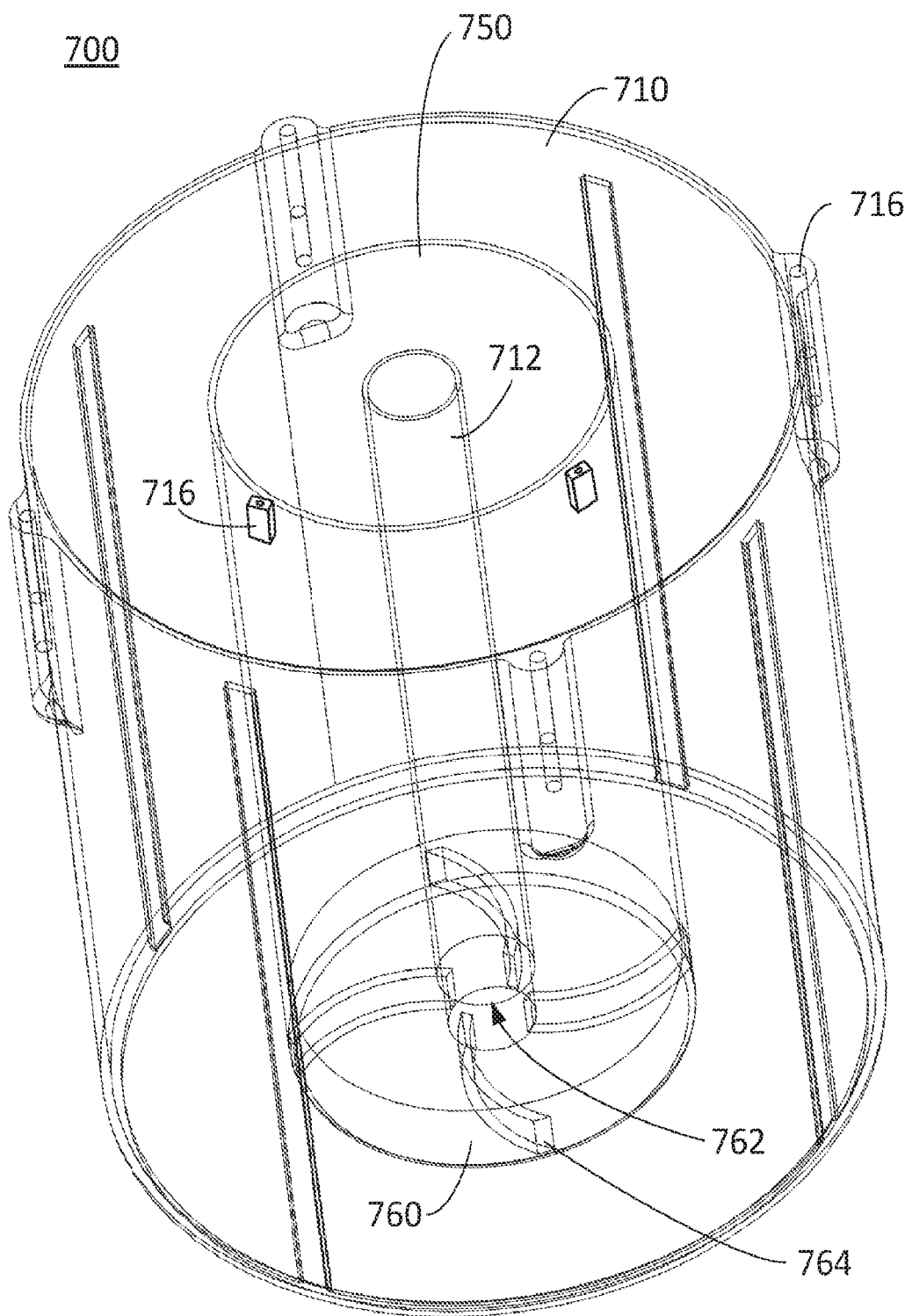
FIG. 7 illustrates a filter system for growing algae according to another embodiment of this disclosure.

FIG. 7 illustrates a filter system 700 for growing algae according to another embodiment of this disclosure. The filter system 700 may include a container 710, an inner core 750, an inlet assembly 712, and a diffuser 760. The container 710 may be a cylindrical container having an opening on one end. The opening of the container 710 may be covered with a lid (not shown in FIG. 7) using fastening portions 716 provided in the top portion of the inner core 750 and/or fastening portions 716 provided in the top portion of the container 710. Bolts in the lid may secure the lid to the inner core 750 and/or the container 710.

The inner core 750 may be disposed inside of the container 710 and approximately in the middle of the container 710 with the side surface of the inner core 750 being parallel to the inner surface of the container 710. The inner core 750 may include a cavity for a light source to be disposed inside the cavity. As shown in FIG. 7, the inlet 712 may be provided in the cavity of the inner core 750. The inlet 712 may include a tube that is provided at approximately at the center of the container 710 and extend in an axial direction of the container 710 and/or an axial direction of the inner core 750. The inlet 712 may be configured to receive water from outside of the container (e.g., via a pump or another filtration system) and provide the water to the diffuser 760. The diffuser 760 may have an opening 762 to receive the inlet 712 and have a plurality of outlets 764 to disperse the water inside of the container.

The diffuser 760 may have a disk-shaped structure having the opening 762 at a top surface of the diffuser 760. The outlets 764 may be provided at the perimeter and side surface of the diffuser 760. The outlets 764 may form cavities inside of the diffuser 760 that radially extend outwardly from the opening 762 provided in the center of the diffuser 760. As shown in FIG. 7, the cavities formed by the outlets 764 may be curved. The curved cavities provide for the water to exit the diffuser 760 at an angle relative to the tangential and radial direction of the diffuser 760 to provide circular flow inside of the container 710. In one embodiment, the outlets 764 may be formed by a straight or curved pipe provided in the diffuser 760.

The inlet 712 and the diffuser 760 may provide an enclosed path for the water to flow inside of the inner core 750 and to provide the water to the area between the inner core 750 and the container 710. The cavity of the inner core 750 may remain without water such that a light source may be provided inside of the cavity. The lid may seal the cavity of the inner core 750 from the water provided between the inner core 750 and the container 710.

Figure 8:
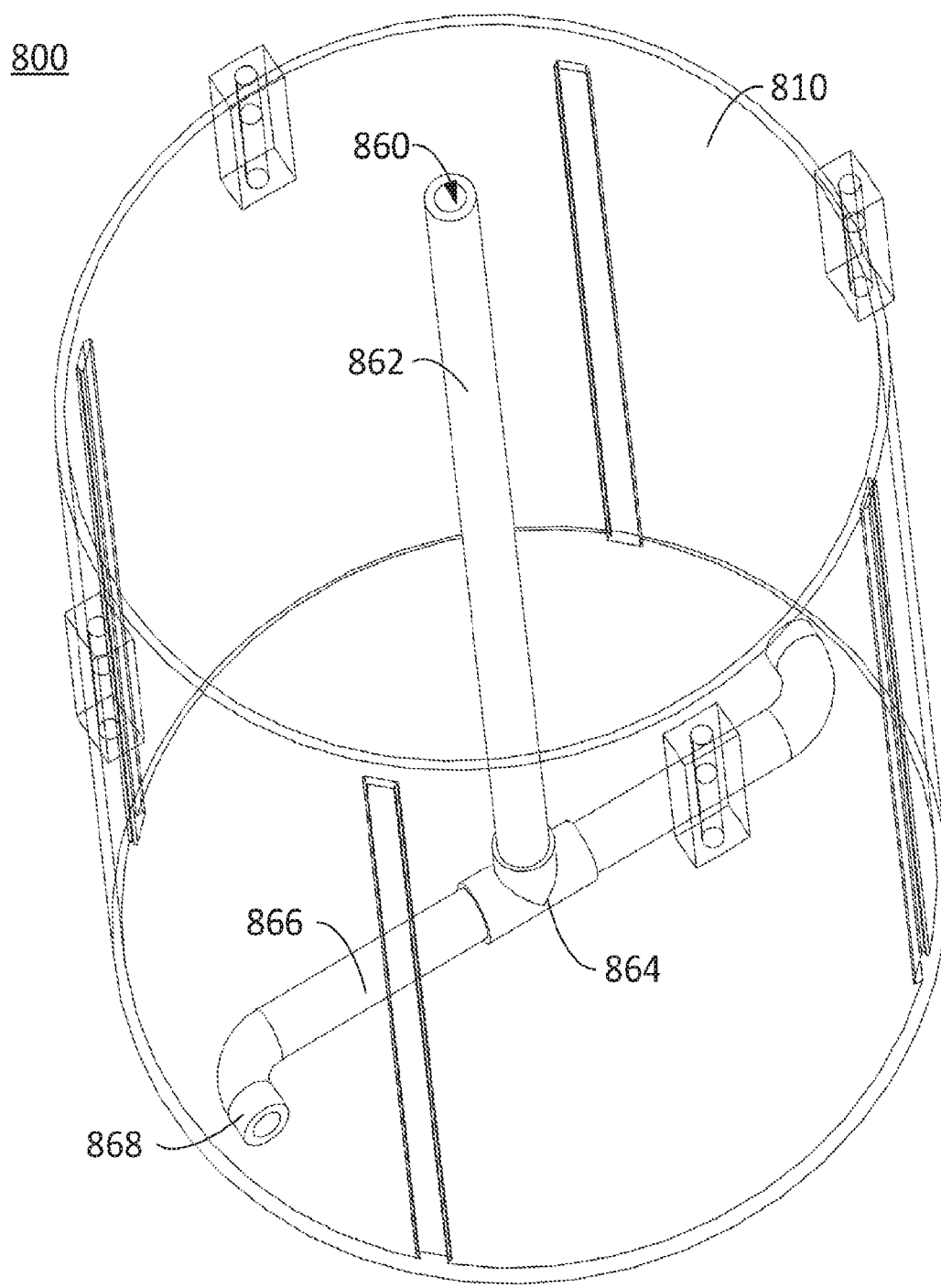
FIG. 8 illustrates a filter system for growing algae according to another embodiment of this disclosure.

FIG. 8 illustrates a filter system 800 for growing algae according to another embodiment of this disclosure. The filter system 800 may include a container 810 with an inlet distributer 860 that distributes the flow of water to different portions within the container 810 to generate circular flow within the container 810. The inlet distributer 860 may receive water from a pump and route the water inside of the container 810. The inlet distributer 860 may include a first pipe 862 routing water received at a first end of the pipe to the bottom of the container 810 from the outside of the container 810. The first pipe 862 may be disposed in approximately the center of the container 810 and extend in an axial direction of the container 810. At a second end of the first pipe 862, a connector 864 may distribute the water to a plurality of secondary pipes 866 extending in a radial direction from the center of the container 810 (e.g., axis of the container 810). An elbow 868 may be provided at ends of each of the secondary pipes 866 to provide circular flow of water in the container 810. The elbow 868 may have an angle of 45 degrees, 90 degrees, and between 45 degrees and 90 degrees. The first pipe 862, the connector 864, and the plurality of secondary pipes 866 may provide a mechanical structure that is rotatable inside of the container 810 due to the water flow.

FIGS. 9A-9C illustrate a filter system 900 for growing algae according to another embodiment of this disclosure. The filter system 900 may include a cylindrical container 910, a lid 920, an inner core 930, an inlet pipe 940, an outlet 922, a distributer 950, and a light source 960. The filter system 900 may further include an exhaust assembly 924, a locking mechanism including at least one latch 926A and a hinge 926B, a lid seal 928, a pipe fitting 942, and/or a ball valve assembly 990.

The cylindrical container 910 may be closed on one end and have an opening on another end. Near the open end of the container 910 a plurality of hinges 926B may be attached to an outside surface of the container 910. A plurality of hinges 926B may be connected to respective latches 926A. The latches 926A and hinges 926B may be configured to secure the lid 920 to the rim of the container 910. A lid seal 928 may be provided in the lid 920 and/or the rim of the container 910 to provide an air and water tight seal between the lid 920 and the container 910.

The lid 920 may include an opening for the inlet pipe 940 and an outlet pipe (not shown in FIG. 9). The inlet pipe 940 and the outlet pipe may be removably coupled to the lid 920 or may be permanently coupled to the lid 920. The lid 920 may include an exhaust assembly 924 to remove air from inside of the container 910. The exhaust assembly 924 may include a fan assembly provided in an opening of the lid 920. In one embodiment, the exhaust assembly 924 may seal the air inside of the container and provide for release of pressure built up in the container 910 when actuated by a user or when the pressure exceeds a predetermined level inside of the container 910.

The inner core 930 may be disposed inside the container 910. The inner core 930 may be a tube made of a clear material (e.g., glass or plastic). In one embodiment, the inner core 930 may be an acrylic tube. The inner core 930 may be disposed approximately in the middle of the container 910 and such that the side surface of the inner core 930 is provided parallel to the side surface of the container 910.

The inner core 930 may be part of the container 910 or may be removably coupled to the bottom surface of the container 910. As shown in FIG. 9, the distributer 950 may be disposed against the bottom surface of the container 910 and provide a recessed portion around the circumference of the distributer 950 to receive the edge of the inner core 930. The inner core 930 and the distributer 950 may be coupled to provide an air and water tight seal. The inner core 930 may be sealed from all sides to avoid water getting inside and damaging the light source 960 disposed inside of the inner core 930. A seal may be provided between the inner core 930 and the lid 920 and/or the inner core 930 may be fixed to the lid 920 to provide the air and water tight seal between the inner core 930 and the lid 920.

The inlet pipe 940 may extend along the vertical axis of the container 910 from outside of the container 910 and towards the bottom of the container 910. The inlet pipe 940 may terminate near the bottom of the container 910 and connect to the distributer 950. The inlet pipe 940 may be a plastic pipe. The pipe fitting 942 may be provided at one end of the inlet pipe 940 to couple the inlet pipe directly or via another tube to a pump supplying the water to the container 910. The inlet pipe 940 may be coupled to an external pipe that routes water pressurized by gravity from a water source (e.g., an aquarium) and to the container 910.

The distributer 950 may include an opening to receive the inlet pipe 940 and a plurality of pipes 952 connecting to the opening and extending in a radial direction from the center of the distributer 950. The plurality of pipes 952 of the distributer 950 may terminate at the edge of the distributer providing outlets 954. The distributer 950 may have a disk-shaped structure having the opening to receive the inlet pipe 940 in the center of the top surface of the distributer 950, and the plurality of pipes 952 terminating at the perimeter and side surface of the distributer 950. The plurality of outlets 954 may be configured to generate circular flow within the container 910 by distributing the water supplied via the inlet pipe 940 to different portions within the container 910 at the bottom surface of the container 910. The plurality of outlets 954 may be configured to release water from the distributer 950 at an angle such that a vortex is created inside of the container 910. In one embodiment, the distributer 950 may be positioned a predetermined distance from the bottom of the container 910. For example, the distributer 950 may be positioned in the middle of the inner core 940. In one embodiment without including the inner core 930 shown in FIG. 9C, the distributer 950 may be allowed to rotate.

The light source 960 may be provided inside of container 910 and/or the inner core 930. As shown in FIGS. 9B and 9C, the light source 960 may be provided adjacent to the inlet pipe 940 and extend along the axial direction of the container. The light source 960 may be wound around the inlet pipe 940.

In one embodiment, the ball valve assembly 990 may be coupled to the outlet 922 in the lid 920. The ball valve assembly 990 may be used to provide water flow in both directions using a single hose.

FIGS. 10A and 10B illustrate a ball valve assembly 1000 according to one embodiment of this disclosure. The ball valve assembly 1000 may include an elongated housing 1010 having a first opening 1012 on one end and a second opening 1014 on an opposite end. A cover 1020 with a cover opening 1022 may be provided to enclose the second opening 1014 of the elongated housing 1010. The cover 1020 may engage the first opening 1014 of the elongated housing 1010 and provide an air and water tight seal (e.g., by a press fit or a thread). A washer (e.g., a rubber washer) may be included between the cover 1020 and the elongated housing 1010 to provide a better seal. The ball valve assembly 1000 may be provided at an outlet (e.g., outlet 922 shown in FIG. 9) to provide air inside and outside of the filter system when a single inlet/outlet (e.g., inlet pipe 940) is used to provide water to the filter system and remove water from the filter system. The ball valve assembly 1000 may be coupled to an outlet of a filtering system via an engaging section 1018 that provides an air and water tight seal.

A first valve ball 1030 and a second valve ball 1040 may be provided inside of the elongated housing 1010 and adjacent to each other. The first valve ball 1030 and the second valve ball 1040 may be made of a material that allows for the first valve ball 1030 and the second valve ball 1040 to float in water. The first valve ball 1030 and the second valve ball 1040 may have a diameter that is smaller than the inside diameter of the elongated housing 1010. A plurality of ridges 1016 may be provided inside the elongated housing 1010 and along the inside wall of the elongated housing 1010 to displace the first valve ball 1030 and/or the second valve ball 1040 from the inside surface of the elongated housing 1010 and to provide a space therebetween. The inside diameter of the elongated housing 1010 near the first opening 1012 may be reduced such that the diameter at the first opening 1012 is made smaller than the diameter of the first valve ball 1030. The ridges 1016 may extend along the reduced diameter portion of the elongated housing 1010 to provide a space between the first valve ball 1030 and the inside surface of the elongated housing 1010. The ridges may allow for a space for water and/or air to travel between the first opening 1012 and the inside of the elongated housing even when the first valve ball 1030 is posited against the ridges 1016 of the elongated housing 1010. The ridges may terminate at the edge of the second opening 1014 of the elongated housing 1010. In one embodiment, one or move grooves may be provided on the inside surface of the elongated housing 1010 to provide a space for water and/or air to travel between the first valve ball 1030/the second valve ball 1040 and the inside surface of the elongated housing 1010.

The cover 1020 may include a sealing portion 1050 that is coupled to the cover opening 1022. The sealing portion 1050 may provide a hemispherical shape that matches the shape of the second valve ball 1040 to provide a seal when the second valve ball 1040 is pressed against the sealing portion 1050. In one embodiment, instead of a sealing portion 1050, the diameter of the elongated housing 1010 may be reduced near the second opening 1014 to provide a seal between the second valve ball 1040 and the elongated housing 1010. An O-ring 1052 may be provided with the sealing portion 1050 to provide a seal between the sealing portion 1050 and the second valve ball 1040.

The ball valve assembly 1000 may allow for bidirectional water exchange between two sources of water via a single inlet/outlet of a filter system and a tank of water, positioned higher than the ball valve assembly 1000 and/or the filtering system. A pump may be coupled to the single inlet/outlet of the filter system and may periodically pumps water such that water from the filtering system is provided to the tank. The tank of water may be provided above the ball valve assembly 1000 and/or the filtering system such that water pressure due to gravity G may be supplied to the filtering system when the pump is not pumping water from the filtering system.

The pump may have a timer that cycles between turning on the pump for a first predetermined time period and turning off the pump for a second predetermined time period. The first predetermined time period may be a time period that is equal to or less than the time it takes for the pump to move all of the water (or a majority of the water) from the filter to the tank. The second predetermined time period may be a time period that is equal to or greater than the time it takes for the water from the display tank to siphon down to the filter due to gravity and fill the filter completely or partially at a predetermined level. In one embodiment, the first predetermined time period may be set such that a portion of the water may remain in the filter before the pump is turned off.

When the filter is filled with water and the pump is turned on for the first predetermined time period, water is taken from the filtering system to the display tank via the single inlet/outlet. During this period of time, as the water is removed from the filter to the tank, the first valve ball 1030 and the second valve ball 1040 may rest against the ridges 1016 or grooves, allowing air to come into the filter through the cover opening 1022. After the first predetermined time period, the pump may turn off to allow water to fill up the filter as the water is moved from the tank to the filter due to gravity via the single inlet/outlet. During this process, before the water fills the filter, the first valve ball 1030 and the second valve ball 1040 may rest on the ridges 1016 or grooves allowing air to leave the filter via the cover opening 1022. When the water fills the filter, the water will start to exit the filter via an outlet coupled to the ball valve assembly 1000 and enter the ball valve assembly via the first opening 1012. As the water fills the ball valve assembly 1000, the first valve ball 1030 and/or the second valve ball 1040 will be caused by the water to be pushed up against the sealing portion 1050, forming an air and water tight seal. Thus water will be prevented from exiting the ball valve assembly 1000 and/or the filter coupled to the ball valve assembly 1000. This process may be repeated to provide a continuous exchange of water between the filter and the tank.

Allowing for two valve balls to be provided inside of the ball valve assembly 1000 allows for the valve balls to maintain a good seal between the second valve ball 1040 and the sealing portion 1050. If only one ball is used inside of the ball valve assembly 1000, the lower half of the valve ball may get dirty as it come in contact with the water and the valve ball may randomly rotate such that the dirty portion of the valve ball will engage the sealing portion 1050 and/or the O-ring 1052, preventing the valve ball from forming a good seal with the sealing portion 1050 and/or the O-ring 1052. Having the first valve ball 1030 and the second valve ball 1040 which are coupled to each other (e.g., glued together) may prevent the valve balls from rotating and allowing for a good seal with the sealing portion 1050 and/or the O-ring 1052 even when a lower portion of the first valve ball 1030 and/or the second valve ball 1040 is dirty.

The ball valve assembly 1000 is not limited to using first valve ball 1030 and/or the second valve ball 1040. Other shapes may be used instead of the first valve ball 1030 and/or the second valve ball 1040. However, using the first valve ball 1030 and/or the second valve ball 1040 will reduce cost because commercial-off-the shelf balls at a low price may be used in the ball valve assembly 1000 instead of custom made objects. The timer controlling the pump may be implemented with a processing system, including a processor, coupled to the pump and/or a pump controller. The processing system may be configured to control the operation of the pump (e.g., timing to turn on the pump, timing to turn off the pump, speed of the water flow generated by the pump). A user interface may be provided to control and set automatic operation of the pump.

FIGS. 11A-11C illustrate a filter system 1100 for growing algae according to another embodiment of this disclosure. The filter system 1100 may include a cylindrical container 1110, a lid 1120, an inner core 1130, an inlet pipe 1140, an outlet 1122, a distributer 1150, a light source 1160, a screen 1170, and a screen retainer 1180. The filter system 1100 may further include a locking mechanism including at least one latch 1126A and a hinge 1126B, a pipe fitting 1142, and lid cover 1190.

The cylindrical container 1110 may be closed on one end and have an opening on another end. Near the open end of the container 1110 a plurality of hinges 1026B may be attached to an outside surface of the container 1110. A plurality of hinges 1126B may be connected to respective latches 1126A. The latches 1126A and hinges 1126B may be configured to secure the lid 1120 to the rim of the container 910. A lid seal (now shown in FIG. 11) may be provided in the lid 1120 and/or the rim of the container 1110 to provide an air and water tight seal between the lid 1120 and the container 1110.

The lid 1120 may include an opening for the inlet pipe 1140 and the outlet 1122. The inlet pipe 1140 and the outlet 1122 may be removably coupled to the lid 1120 or may be permanently coupled to the lid 1120. The lid 1120 may include an exhaust assembly to remove air from inside of the container 1110.

The inner core 1130 may be disposed inside the container 1110. The inner core 1130 may be a tube made of a clear material (e.g., glass or plastic). In one embodiment, the inner core 1130 may be an acrylic tube. The inner core 1130 may be disposed approximately in the middle of the container 1110 and such that the side surface of the inner core 1130 is provided parallel to the side surface of the container 1110.

The inner core 1130 may be part of the container 1110, may be removably coupled to the bottom surface of the container 1110, or maybe removably or permanently coupled to the lid 1120. As shown in FIG. 11, the distributer 1150 may be disposed against the bottom surface of the container 1110 and provide a recessed portion around the circumference of the distributer 1150 to receive the edge of the inner core 1130. The inner core 1130 and the distributer 1150 may be coupled to provide an air and water tight seal. The distributer 1150 may also be coupled to the inlet pipe 1140 to provide an air and water tight seal. The inner core 1130 may be sealed from all sides to avoid water getting inside and damaging the light source 1160 disposed inside of the inner core 1130. A seal may be provided between the inner core 1130 and the lid 1120 and/or the inner core 1130 may be fixed to the lid 1120 to provide the air and water tight seal between the inner core 1130 and the lid 1120.

The screen 1170 may be disposed inside of the container 1110 between the inner side surface of the container 1110 and the outside surface of the inner core 1130, to split the water volume inside the container into two concentric cylindrical volumes. For example, the screen 1170, may be provided a certain distance away from the inner side surface of the container 1110 and a certain distance away from the outside surface of the inner core 1130. In one embodiment, the screen 1170 may be disposed inside of the container 1110 such that the screen 1170 is the same distance away from the inside side surface of the container 1110 and the outside surface of the inner core 1130. The screen 1170 may include one or more sections, each section having a flat surface which is provided parallel to the inner side surface of the container 1110 and/or the outside surface of the inner core 1130. The screen may be provided against the inner side surface of the container 1110 or a predetermined distance away from the inner side surface of the container 1110. The screen retainer 1180 may be provided near the rim of the container 1110 to secure the one or more screens 1170 in place. The screen retainer 1180 may have a circular shape with a grove into which one edge of the screen(s) 1170 is provided. The screen retainer 1180 may secure the screen(s)

1170 against and/or near the inside side surface of the container 1110 such that the screen(s) 1170 does not move when circular flow of water is generated inside of the container 1110. A groove in the bottom of the container 1110 may be provided to secure the screen 1170 in place near the bottom of the container 1110. The groove in the bottom of the container and/or the screen retainer 1180 may position the screen at the desired location in the container 1110 between the insider surface of the container 1110 and the inner core 1130. The screen retainer 1180 may be removably coupled to the inner side of the container 1110 or to the lid 1120.

The inlet pipe 1140 may extend along the vertical axis of the container 1110 from outside of the container 1110 and towards the bottom of the container 1110. The inlet pipe 1140 may terminate near the bottom of the container 1110 and connect to the distributer 1150. The inlet pipe 1140 may be a plastic pipe. The pipe fitting 1142 may be provided at one end of the inlet pipe 1140 to couple the inlet pipe directly or via another tube to a pump supplying the water to the container 1110.

The distributer 1150 may include an opening to receive the inlet pipe 1140 and a plurality of pipes 1152 connecting to the opening and extending in a radial direction from the center of the distributer 1150. The plurality of pipes 1152 of the distributer 1150 may terminate at the edge of the distributer providing outlets 1154. The distributer 1150 may have a disk-shaped structure having the opening to receive the inlet pipe 1140 in the center of the top surface of the distributer 1150, and the plurality of pipes 1152 terminating at the perimeter and side surface of the distributer 1150. The plurality of outlets 1154 may be configured to generate circular flow within the container 1110 by distributing the water supplied via the inlet pipe 1140 to different portions within the container 1110 at the bottom surface of the container 1110. The plurality of outlets 1154 may be configured to release water from the distributer 1150 at an angle such that a vortex is created inside of the container 910.

The light source 1160 may be provided inside of container 1110 and/or the inner core 1130. As shown in FIGS. 11B and 11C, the light source 1160 may be provided adjacent to the inlet pipe 1140 and extend along the axial direction of the container 1110. The light source 1160 may be would around the inlet pipe 1140. In one embodiment, the light source 1160 may be wound around a pipe (e.g., an LED pipe) that has an inner diameter bigger than an outer diameter of the inlet pipe 1140 such that the LED pipe can be removably placed over the inlet pipe 1140. Since no part of the LED pipe comes into contact with the water, it can be made of any type of material, especially one that can conduct and dissipate the heat from the LED strip to the surrounding air.

The lid 1120 may be a transparent lid to allow light to enter the container 1110 from the outside of the container 1120 and/to allow for inspection of the inside of the container 1110 without having to remove the lid 1120. One or more lid covers 1190 may be provided on a surface of the lid 1120 to prevent light from the light source 1160 from exiting the inside of the container 1110. The lid cover(s) 1190 may have a reflective surface on at least one side to reflect light back into the container. In one embodiment, a lid cover 1190 may be provided over an opening in the lid 1120 that is not transparent to allow for inspection of the inside of the container 1110 without removing the lid 1120.

Figure 12:
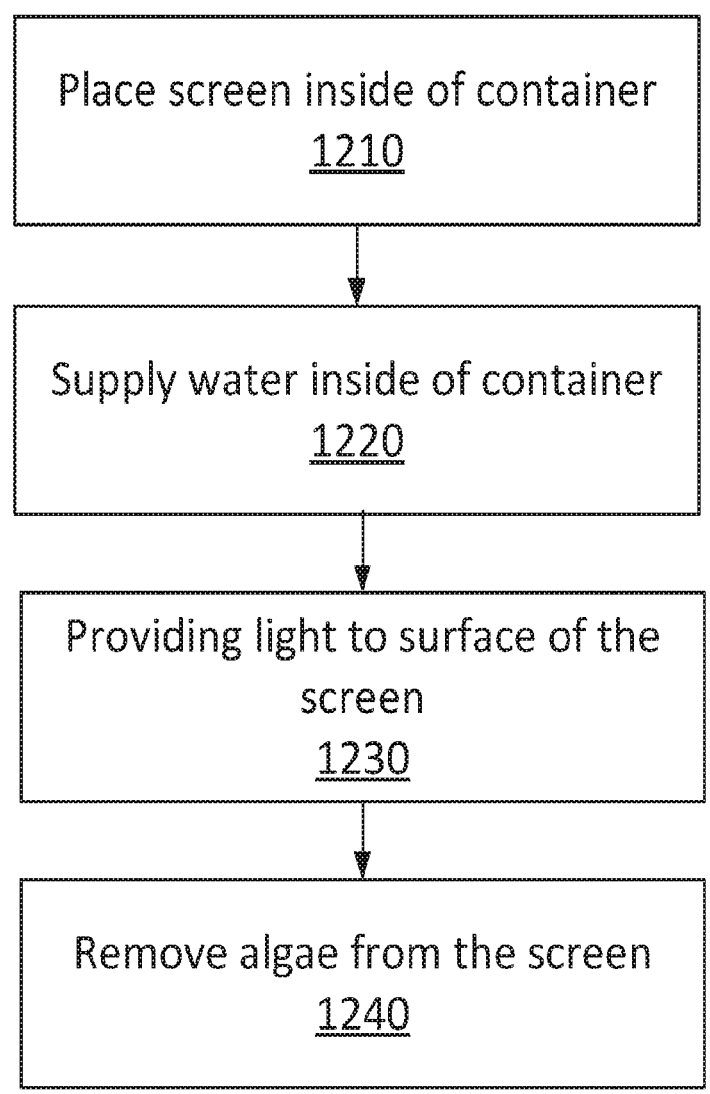
FIG. 12 illustrates a method of growing algae in a filtration system according to an embodiment of this disclosure.

FIG. 12 illustrates a method 1200 of growing algae in a filtration system according to an embodiment of this disclosure. The method 1200 may include placing one or more screens inside of a container 1210, supplying water inside of the container 1220, providing light to a surface of the screen 1230, and removing algae from the surface of the screen 1240.

The one or more screens may be placed inside of a cylindrical container such that the surface of the screens is provided against the inside surface of the cylindrical container. The screen(s) may be secured via grooves provided on the surface of the cylindrical container or via a screen retainer that secures the screens on the edges of the screen at the bottom of the container and/or at the top of the container. The screen(s) may cover a portion of the complete inside surface of the cylindrical container. Screens may be provided such that at least some portions of the screens overlap.

The water may be supplied inside of the container via a pump provided inside or outside of the container. The pump may push a portion of the water inside the container to create an entrainment effect to create a generally circular or spiral flow of water inside the container and over the surface of the screen(s). An inlet may be provided near the bottom of the container to push a portion of the water near the bottom of the container in a circular direction. One or more outlets may be provided inside of the container to direct the water flow in the circular direction.

The light source may be provided inside of the container to provide light to the surface of the screen that is opposite of the inside surface of the container. The light source may be a submersible light source or may be provided inside a housing (e.g., inside an inner core having a cavity) that is disposed inside of the container. The light source may be an LED strip light. The light source may be provided outside of the container and a light conductor may guide light to the inside of the filter. The light source may be set to periodically turn off and on manually or automatically via a timer to optimize the algae growth. The time may be implemented via a processing system including a processor.

The presence of light and flow of water will encourage algae to grow on the surface of the screen. As the screen gets filled up with algae, the algae may be removed from surface of the screen to allow for more algae to grow. Removing the algae may prevent old algae from dying because the old algae does not receive sufficient light from the light source.

While the various embodiments discussed above utilize growing algae on a surface, other plants and photo synthesizing organisms may be encouraged to grow on the surface to filter the water. In some embodiments, the screen may be seeded with the algae. In some embodiment, genetically engineered algae that is designed to enhance the filtration of the water may be provided on the screen.

Reference in the specification to "one embodiment" or "an embodiment" means that a particular feature, structure, or characteristic described in connection with the embodiment may be included in at least an implementation. The appearances of the phrase "in one embodiment" in various places in the specification may or may not be all referring to the same embodiment. In addition, some part/components discussed above may be combined and/or separated to provide the same and/or different parts. For example, one or more parts/components may be provided as a single part by manufacturing a single part (e.g., by 3D printing).

Also, in the description and claims, the terms "coupled" and "connected," along with their derivatives, may be used. In some embodiments of the invention, "connected" may be used to indicate that two or more elements are in direct physical contact with each other. "Coupled" may mean that two or more elements are in direct physical contact. However, "coupled" may also mean that two or more elements may not be in direct contact with each other, but may still cooperate or interact with each other.

Thus, although embodiments of the invention have been described in language specific to structural features and/or methodological acts, it is to be understood that claimed subject matter may not be limited to the specific features or acts described. Rather, the specific features and acts are disclosed as sample forms of implementing the claimed subject matter.

In the above description, numerous specific details are set forth to provide a thorough understanding of embodiments of the invention. The invention is capable of other embodiments and of being practiced and carried out in various ways. One skilled in the relevant art will recognize, however that the invention can be practiced without one or more of the specific details or with other methods, components, techniques, etc. In other instances, well-known operations or structures are not shown or described in details to avoid obscuring aspects of the invention. Also, it is to be understood that the phraseology and terminology employed herein are for the purpose of the description and should not be regarded as limited.

Although the processes illustrated and described herein include series of steps, it will be appreciated that the different embodiments of the present invention are not limited by the illustrated ordering of steps, as some steps may occur in different orders, some concurrently with other steps apart from that shown and described herein. In addition, not all illustrated steps may be required to implement a methodology in accordance with the present invention. Moreover, it will be appreciated that the processes may be implemented in association with the apparatus and systems illustrated and described herein as well as in association with other systems not illustrated.

We claim:

1. A system for growing algae, the system comprising:
    a container including an inlet for providing water into the container;
    an outlet for removing water from the container;
    a light source or a light conductor providing light for a surface on which algae grows inside the container, wherein the surface is a removable screen or mesh having a planar surface positioned against an inner surface of the container; and
    a vortex generating mechanism configured to induce an entrainment effect in at least a portion of water in the container, the entrainment effect moving the water in the container to create a generally circular or spiral flow of water inside the container and over the surface,
    wherein the vortex generating mechanism comprises:
        a static mechanical structure coupled to the inlet and disposed inside the container and configured to receive the water flow and output the water inside the container in a generally horizontal direction generally tangential to the generally circular or spiral flow of water; or
        a dynamic mechanical structure configured to rotate inside the container.

2. The system of claim 1 comprising the static mechanical structure configured to output the water inside the container in the generally horizontal direction generally perpendicular to a vertical central axis of the container.

3. The system of claim 1 comprising the dynamic mechanical structure configured to receive and output the water inside the container in a generally horizontal direction generally perpendicular to a vertical central axis of the container.

4. The system of claim 1, wherein the vortex generating mechanism comprises the static mechanical structure and the static mechanical structure includes a distributer assembly providing a plurality of distributor outlets configured to output the water flow at different locations inside the container, each distributor outlet of the plurality of distributor outlets outputting the water flow in a generally horizontal direction generally tangential to the generally circular or spiral flow of water.

5. A system for growing algae, the system comprising:
    a container including an inlet for providing water into the container;
    an outlet for removing water from the container;
    a light source or a light conductor providing light for a surface inside the container;
    a vortex generating mechanism configured to induce an entrainment effect in at least a portion of water in the container, the entrainment effect moving the water in the container to create a generally circular or spiral flow of water inside the container and over the surface,
    wherein the vortex generating mechanism comprises:
        a static mechanical structure coupled to the inlet and disposed inside the container and configured to receive the water flow and output the water inside the container in a generally horizontal direction generally tangential to the generally circular or spiral flow of water; or
        a dynamic mechanical structure configured to rotate inside the container; and
    a ball valve assembly configured to remove air from inside of the container and a lid covering the container, the lid including the outlet to which the ball valve assembly is configured to couple, the ball valve assembly including: an elongated housing including one open end configured to connect to the outlet provided in the lid, two valve balls directly coupled to one another and disposed inside of the elongated housing such that they are movable inside of the elongated housing without sealing the open end of the elongated housing coupled to the outlet, and a cover enclosing the other open end of the elongated housing, the cover including an opening and a sealing portion next to the opening, the sealing portion allowing for a seal between the sealing portion and one of the valve balls when the valve ball is positioned against the sealing portion.

6. The system of claim 1 further comprising:
    a clear core disposed inside the container, the clear core including a cavity, and wherein the light source or the light conductor is disposed inside the cavity of the clear core.

7. The system of claim 1 wherein the container has a generally cylindrical inner surface and an opening at one end of the container; the system further comprising: a watertight lid covering the opening of the container.

8. The system of claim 1 including the light source, wherein the light source is an LED strip light.

9. The system of claim 1, that is used as a bioremediation water filtering apparatus.

10. The system of claim 1, wherein the vortex generating mechanism includes a pressurizing mechanism that affects water inside the container.

11. The system of claim 10, wherein the pressurizing mechanism comprises a pump or is configured to use gravity.

12. The system of claim 1, wherein the surface is a disposed inside the container such that the planar surface of the removable screen or mesh is parallel to an inner surface of the container.

13. The system of claim 1, wherein the surface extends linearly along an axis about which the generally circular or spiral flow moves.

14. The system of claim 1 further comprising an exhaust assembly configured to remove air from inside of the container.

15. A system for growing algae, the system comprising:
- a container including an inlet for providing water into the container;
- an outlet for removing water from the container;
- a light source or a light conductor providing light for a surface inside the container; and
- a vortex generating mechanism configured to induce an entrainment effect in at least a portion of water in the container, the entrainment effect moving the water in the container to create a generally circular or spiral flow of water inside the container and over the surface, wherein the vortex generating mechanism comprises:
- a static mechanical structure coupled to the inlet and disposed inside the container and configured to receive the water flow and output the water inside the container in a generally horizontal direction generally tangential to the generally circular or spiral flow of water, wherein the container includes a clear central core including a tubular cavity aligned with a central axis of the container and the static mechanical structure is disposed inside the container and includes (1) an inlet pipe disposed inside of the cavity of the clear central core and configured to receive water from the inlet and (2) a plurality of distributor outlets configured to distribute the water received from the inlet via the inlet pipe at different locations near a bottom surface of the container.

16. The system of claim 15, wherein the container includes a generally cylindrical inner surface and each of the plurality of distributor outlets is disposed adjacent to the inner surface of the container.

17. The system of claim 15, wherein each of the plurality of distributor outlets is disposed at an outer surface of the clear central core.

* * * * *